US00PP27997P2

(12) United States Plant Patent
Miyazaki

(10) Patent No.: US PP27,997 P2
(45) Date of Patent: May 9, 2017

(54) ***PETUNIA* PLANT NAMED 'SUNSURF YOHAIHA'**

(50) Latin Name: *Petunia×hybrida*
Varietal Denomination: Sunsurf Yohaiha

(71) Applicant: SUNTORY FLOWERS LIMITED, Tokyo (JP)

(72) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 14/998,487

(22) Filed: Jan. 9, 2016

(51) Int. Cl.
*A01H 5/02* (2006.01)

(52) U.S. Cl.
USPC ..... Plt./356.1

(58) Field of Classification Search
USPC ..... Plt./356.1
CPC ..... A01H 5/025
See application file for complete search history.

*Primary Examiner* — Kent L Bell
(74) *Attorney, Agent, or Firm* — C. A. Whealy

(57) ABSTRACT

A new and distinct cultivar of *Petunia* plant named 'Sunsurf Yohaiha', characterized by its large upright and mounding to semi-trailing plant habit; vigorous growth habit; freely branching habit; freely flowering habit; long flowering period; relatively large flowers that are pale pink in color with dark violet-colored venation and centers; and good garden performance and high temperature tolerance.

1 Drawing Sheet

Botanical designation: *Petunia×hybrida.*
Cultivar denomination: ' SUNSURF YOHAIHA'.

BACKGROUND OF THE INVENTION

The present invention relates to a new and distinct cultivar of *Petunia* plant, botanically known as *Petunia×hybrida* and hereinafter referred to by the name 'Sunsurf Yohaiha'.

The new *Petunia* plant is a product of a planned breeding program conducted by the Inventor in Higashiomi, Shiga, Japan. The objective of the breeding program is to create new vigorous and freely-flowering *Petunia* plants with large attractive flowers.

The new *Petunia* plant originated from a cross-pollination made by the Inventor in July, 2012 in Higashiomi, Shiga, Japan of a proprietary selection of *Petunia×hybrida* identified as code designation 054C-1, not patented, as the female, or seed, parent with a proprietary selection of *Petunia×hybrida* identified as code designation Px5315-03, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in July, 2013.

Asexual reproduction of the new *Petunia* plant by terminal cuttings in a controlled greenhouse environment in Higashiomi, Shiga, Japan since January, 2014 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunsurf Yohaiha'. These characteristics in combination distinguish 'Sunsurf Yohaiha' as a new and distinct *Petunia* plant:

1. Large upright and mounding to semi-trailing plant habit.
2. Vigorous growth habit.
3. Freely branching habit.
4. Freely flowering habit.
5. Long flowering period.
6. Relatively large flowers that are pale pink in color with dark violet-colored venation and centers.
7. Good garden performance and high temperature tolerance.

Plants of the new *Petunia* can be compared to plants of the female parent selection. Plants of the new *Petunia* differ primarily from plants of the female parent selection in flower color as plants of the female parent selection have bright red purple-colored flowers.

Plants of the new *Petunia* can be compared to plants of the male parent selection. Plants of the new *Petunia* differ primarily from plants of the male parent selection in the following characteristics:

1. Plants of the new *Petunia* are larger than plants of the male parent selection.
2. Plants of the new *Petunia* have larger flowers than plants of the male parent selection.
3. Plants of the new *Petunia* and the male parent selection differ in flower color as plants of the male parent selection have white-colored flowers.

Plants of the new *Petunia* can also be compared to plants of the *Petunia×hybrida* 'Sunbui Mirehaha', disclosed in U.S. Plant patent application Ser. No. 13/998,606. In side-by-side comparisons conducted in Higashiomi, Shiga, Japan, plants of the new *Petunia* and 'Sunbui Mirehaha' differed primarily in the following characteristics:

1. Leaves of plants of the new *Petunia* were elliptic in shape whereas leaves of plants of 'Sunbui Mirehaha' were ovate in shape.
2. Plants of the new *Petunia* were more freely flowering than plants of 'Sunbui Mirehaha'.
3. Flowers of plants of the new *Petunia* were larger than flowers of plants of 'Sunbui Mirehaha'.
4. Plants of the new *Petunia* and 'Sunbui Mirehaha' differed in flower color as plants of 'Sunbui Mirehaha' had flowers that were bright red purple in color.
5. Plants of the new *Petunia* had broader sepals than plants of 'Sunbui Mirehaha'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurf Yohaiha' grown in a container.

The photograph at the bottom of the sheet is a close-up view of a typical flowering plant of 'Sunsurf Yohaiha'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were six months old when the photographs and description were taken. In the following description, color references are made to The Royal Horticultural Society Colour Chart, 2007 Edition, except where general terms of ordinary dictionary significance are used.

Botanical classification: *Petunia×hybrida* 'Sunsurf Yohaiha'.

Parentage:

*Female, or seed, parent*.—Proprietary selection of *Petunia×hybrida* identified as code designation 054C-1, not patented.

*Male, or pollen, parent*.—Proprietary selection of *Petunia×hybrida* identified as code designation Px5315-03, not patented.

Propagation:

*Type*.—By terminal cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant form and growth habit*.—Large upright and mounding to semi-trailing plant habit; freely branching habit with numerous lateral branches developing per plant; pinching enhances lateral branch development; vigorous growth habit.

*Plant height*.—About 41 cm.

*Plant diameter*.—About 91 cm.

Lateral branch description:

*Length*.—About 37 cm.

*Diameter*.—About 1.9 mm.

*Internode length*.—About 2.1 cm.

*Strength*.—Strong, flexible.

*Aspect*.—Mostly upright to outwardly.

*Texture*.—Densely pubescent; rough.

*Color*.—Close to 144B.

Leaf description:

*Arrangement*.—Alternate, simple.

*Length*.—About 3.3 cm.

*Width*.—About 1.8 cm.

*Shape*.—Elliptic.

*Apex*.—Broadly acute.

*Base*.—Attenuate.

*Margin*.—Entire.

*Texture, upper and lower surfaces*.—Densely pubescent; rough; viscid.

*Venation pattern*.—Pinnate; reticulate.

*Color*.—Developing leaves, upper surface: Close to 143B. Developing leaves, lower surface: Close to 143C. Fully expanded leaves, upper surface: Close to 143A; venation, close to 144B. Fully expanded leaves, lower surface: Close to 143C; venation, close to 144C.

*Petioles*.—Length: About 3.9 mm. Diameter: About 1.7 mm. Texture, upper and lower surfaces: Pubescent; viscid. Color, upper and lower surfaces: Close to 144B.

Flower description:

*Flower arrangement and habit*.—Single-type salver-form flowers arising from upper leaf axils; freely flowering habit with usually about 230 flowers developing per plant during the flowering season; flowers face mostly upright to outwardly.

*Fragrance*.—None detected.

*Natural flowering season*.—Plants of the new *Petunia* initiate and develop flowers about seven weeks after planting; long flowering period, flowering commences naturally during the spring and plants flower continuously throughout the summer until late autumn in Japan.

*Flower longevity*.—Individual flowers last about seven to ten days on the plant; flowers not persistent.

*Flower buds*.—Length: About 3.65 cm. Diameter: About 9.9 mm. Shape: Cylindrical. Color: Close to N77B; towards the apex, close to 69A.

*Flower diameter*.—About 6.5 cm.

*Flower length (depth)*.—About 1.6 cm.

*Flower tube length*.—About 3.3 cm.

*Flower tube diameter, proximally*.—About 3.4 mm.

*Flower tube diameter, distally*.—About 1.6 cm.

*Corolla*.—Quantity and arrangement: Five in a single whorl, fused at the base and opening into a flared trumpet. Petal length from throat: About 2.8 cm. Petal width: About 3.2 cm. Petal shape: Roughly spatulate. Petal apex: Mucronate. Petal margin: Entire; slightly undulate. Petal texture, upper and lower surfaces: Smooth, glabrous; velvety. Throat texture: Smooth, glabrous. Tube texture: Pubescent. Color: Petal, when opening, upper surface: Close to 62D; at the margin, close to 64C. Petal, when opening, lower surface: Close to 69D; at the margin, close to 70B. Petal, fully opened, upper surface: Close to 69D; at the margin, close to 68B; at the throat, close to 67B; venation, close to 59C; color does not change with development. Petal, fully opened, lower surface: Close to N155B; midvein, close to NN155A; at the margin, close to N74C; color does not change with development. Throat: Close to 83B to 83C; venation, close to 83A. Tube: Close to 79C.

*Calyx*.—Arrangement: One star-shaped calyx tube with five sepals in a single whorl and fused at the base. Sepal length: About 1.3 cm. Sepal width: About 6.2 mm. Sepal shape: Lanceolate to elliptic. Sepal apex: Acute. Sepal margin: Entire. Sepal texture, upper and lower surfaces: Pubescent; viscid. Color, upper surface: Close to 143A. Color, lower surface: Close to 144A.

*Peduncles*.—Length: About 1.7 cm. Diameter: About 1.7 mm. Strength: Strong, flexible. Aspect: Upright to outwardly. Texture: Pubescent; viscid. Color: Close to 145A.

*Reproductive organs*.—Stamens: Quantity per flower: Five. Filament length: About 1.8 cm. Filament color: Distally, close to NN155C; mid-section, close to N81C; proximally, close to NN155B. Anther shape: Ellipsoidal. Anther size: About 1.7 mm by 2 mm. Anther color: Close to 92B. Pollen amount: Moderate. Pollen color: Close to 79A. Pistils: Quantity per flower: One. Pistil length: About 1.8 cm. Style color: Distally, close to 86C; proximally, close to 145D. Stigma shape: Transversely ellipsoidal. Stigma color: Close to 86B. Ovary color: Close to 145B. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunsurf Yohaiha' as illustrated and described.

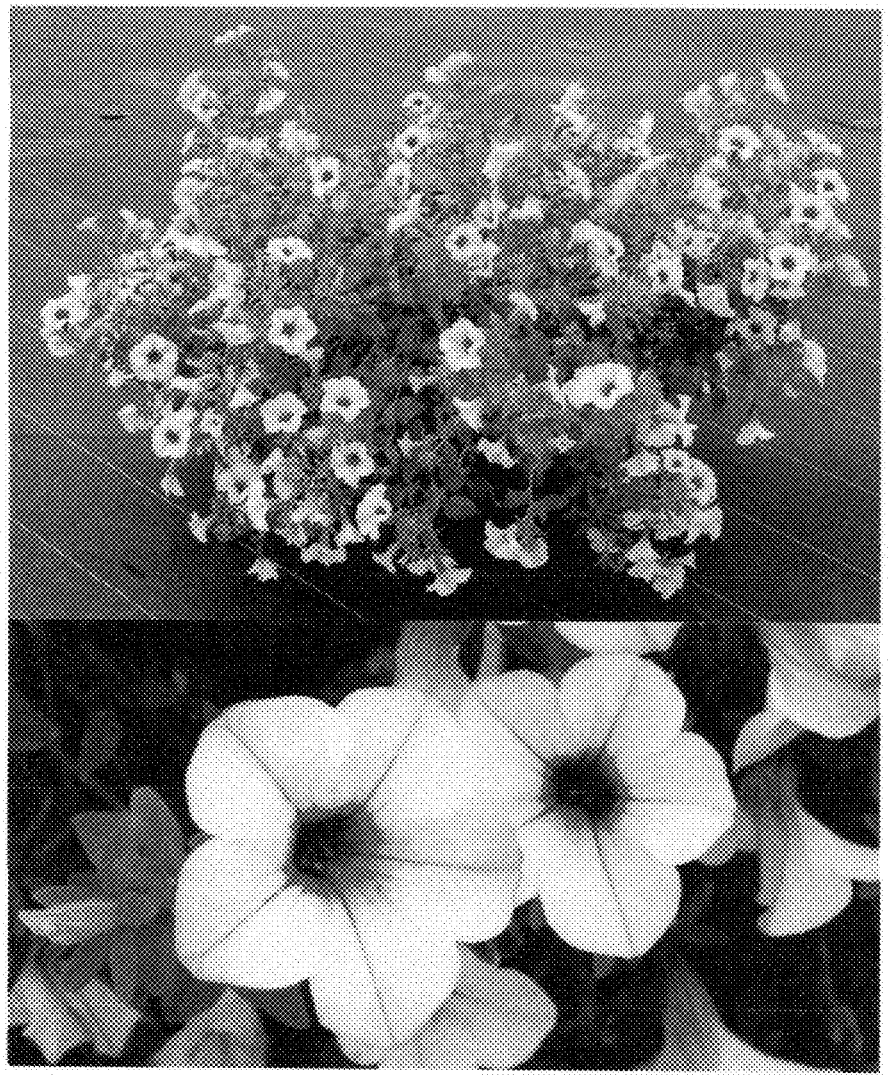

* * * * *